US008512044B2

(12) United States Patent
Sakezles (10) Patent No.: US 8,512,044 B2
(45) Date of Patent: Aug. 20, 2013

(54) DIELECTRIC PROPERTIES MODELS AND METHODS OF USING SAME

(76) Inventor: Christopher Sakezles, Sarasota, FL (US)

( * ) Notice: Subject to any disclaimer, the term of this patent is extended or adjusted under 35 U.S.C. 154(b) by 0 days.

(21) Appl. No.: 13/423,861

(22) Filed: Mar. 19, 2012

(65) Prior Publication Data
US 2012/0276510 A1     Nov. 1, 2012

Related U.S. Application Data

(60) Division of application No. 11/608,855, filed on Dec. 11, 2006, now Pat. No. 8,137,110, which is a continuation-in-part of application No. 11/172,575, filed on Jun. 30, 2005, now Pat. No. 7,507,092, which is a continuation-in-part of application No. 11/098,248, filed on Apr. 4, 2005, now Pat. No. 7,272,766, which is a continuation-in-part of application No. 11/050,161, filed on Feb. 3, 2005, now Pat. No. 7,427,199.

(60) Provisional application No. 60/750,203, filed on Dec. 14, 2005.

(51) Int. Cl.
*G09B 23/28* (2006.01)

(52) U.S. Cl.
USPC ................................................ 434/267

(58) Field of Classification Search
USPC ................... 434/262, 267, 270, 272, 274
See application file for complete search history.

(56) References Cited

U.S. PATENT DOCUMENTS

| 3,802,096 | A | 4/1974 | Matern |
| 6,474,993 | B1 | 11/2002 | Grund et al. |
| 6,997,719 | B2 | 2/2006 | Wellman et al. |
| 7,255,565 | B2 | 8/2007 | Keegan |
| 7,549,866 | B2 | 6/2009 | Cohen et al. |
| 2003/0044758 | A1 | 3/2003 | Ray |
| 2003/0198925 | A1 | 10/2003 | Dowell |
| 2004/0126746 | A1* | 7/2004 | Toly ............................... 434/262 |
| 2005/0100873 | A1 | 5/2005 | Meythaler et al. |
| 2005/0106545 | A1* | 5/2005 | Heruth et al. ................. 434/267 |
| 2007/0148626 | A1 | 6/2007 | Ikeda |

FOREIGN PATENT DOCUMENTS

| WO | WO 00/21435 A1 | 4/2000 |
| WO | WO 01/54575 A1 | 8/2001 |
| WO | WO 01/62194 A1 | 8/2001 |

OTHER PUBLICATIONS

The Effects of Testing Environment on the Viscoelastic Properties of Soft Tissues, Mark P. Ottensmeyer et al., ISMS 2004.
"Measuring In Vivo Animal Soft Tissue Properties for Haptic Modeling in Surgical Simulation," Iman Brouwer et al., Medicine Meets Virtual Reality 2001, J. D. Westwood et al.

* cited by examiner

*Primary Examiner* — Kurt Fernstrom
(74) *Attorney, Agent, or Firm* — Timothy H. Van Dyke; Beusse Wolter (57) ABSTRACT

Disclosed herein are dielectric properties models that are designed to enable simulated use testing by medical device companies, medical device designers, individual inventors, or any other entity interested in the performance of medical devices. These models are unique in possessing a level of correlation to dielectric properties of human or nonhuman animal tissues that allows them to be substituted for either a live animal, an animal cadaver, or a human cadaver in the testing of these devices. These models are further characterized by a similarity of geometry, individual component physical properties, and component-to-component interfacial properties with the appropriate target tissue and anatomy.

3 Claims, 4 Drawing Sheets

DIELECTRIC PROPERTIES MODELS AND METHODS OF USING SAME

CROSS-REFERENCE TO RELATED APPLICATIONS

This application is a divisional application of U.S. patent application Ser. No. 11/608,855 filed Dec. 11, 2006; now U.S. Pat. No. 8,137,110 which is a continuation-in-part application to U.S. patent application Ser. No. 11/172,575; filed Jun. 30, 2005; now U.S. Pat. No. 7,507,092 which is a continuation-in-part application to U.S. patent application Ser. No. 11/098,248; filed Apr. 4, 2005, now U.S. Pat. No. 7,272,766 which is a continuation in part application to U.S. patent application Ser. No. 11/050,161, filed Feb. 3, 2005. now U.S. Pat. No. 7,427,199 This application claims the benefit of priority to foregoing under 35 USC 120, and the teachings of such applications is hereby incorporated herein.

This application also claims the benefit of U.S. Ser. No. 60/750,203 filed Dec. 14, 2005, incorporated herein in its entirety by reference

BACKGROUND OF THE INVENTION

During the development of any new medical device, various tests may be required, including the characterization of physical properties (geometric, mechanical, electrical, electromagnetic, thermal, chemical, etc), the evaluation of overall device performance (numerical simulation or simulated use testing), or testing to determine the effect of the device on living tissues. These development tests may be broadly classified as either biological tests, theoretical tests, or physical tests, although there are areas where these testing classes overlap one another.

Biological testing generally involves an analysis of the interaction between the device and human or animal tissues. The biological tests that are performed first are generally biocompatibility tests, which evaluate the tendency of the device to cause damage to living tissues by mere presence of the materials comprising the device. Later on in the development cycle, the device may be tested in a live animal (animal study) or a human patient (clinical trial) to determine the ability of the device to perform its intended use and to evaluate safety and efficacy (device performance). Animal studies represent a special type of test known as simulated use testing, so called because the animal is a simulation of the actual use (human) environment.

Theoretical or computational tests may include finite element analysis, kinematic analysis, and computational fluid dynamics. These tests employ knowledge of the physical properties (strength, mass, density, viscosity, etc) of the device and actual use environment to construct a computer model of the device—tissue system. This type of model may then be used to predict device performance, the tendency of the device to fail, and possibly the tendency of the device to cause injury. Of course, these models are limited by the assumptions made in their derivation and the computational power of the computer. Unfortunately, it may be difficult to quantitatively describe a device, and more importantly the actual use environment, in sufficient detail to yield realistic results.

Physical testing essentially evaluates the design of the device. That is, this physical testing may involve; (1) the measurement of device geometry such as lengths, diameters, and wall thicknesses, (2) the measurement of mechanical properties such as tensile strength and stiffness, (3) the measurement of other device characteristics such as color, thermal conductivity, dielectric properties or other properties, or (4) simulation testing involving trial use of the device in some model of the actual use environment. The purpose of this simulation testing is to evaluate the safety (tendency to injure) and efficacy (performance characteristics) of the device, and in general to evaluate the ability of the device to perform it's intended use. As previously stated, animal studies are one important form of simulation test. Other vehicles (the simulated environment) for this type of testing include cadavers (both human and animal) and benchtop fixtures, which are man-made representations of a particular target anatomy.

The new FDA quality system regulation (QSR) now requires testing under simulated or actual use conditions for all nonexempt Class II and Class III medical devices. Not all manufacturers perform actual use (human clinical trial) testing for every medical device, so in these cases simulation testing is definitely a requirement. At least four traditional simulation options are available to meet this requirement, each with its own advantages and drawbacks. These four general approaches (Table I) to simulation testing involve theoretical (computer) models, benchtop (physical) models, cadaver (human or animal) models, and live animal model % Once again, human subjects are also employed in the development of many medical devices, but since humans represent the actual use environment, these tests (clinical studies) are not considered simulation tests.

TABLE I

The four general approaches to simulation testing including the environment and models involved.

| Theoretical Model | Benchtop Model | Cadaver Model | Live Animal |
|---|---|---|---|
| In vitro | In vitro | In vitro | In vivo |
| Theoretical or computational model | Physical properties model | Human or animal cadaver | Animal study |

Typical medical device development schemes generally involve testing early prototypes in simple bench top test fixtures. Feedback from these tests shape the product through design revisions that are subsequently evaluated using the same model. However, since this process is iterative, as the design matures the models that are needed generally become more complex. For example, a new coronary catheter may undergo initial testing in simple plastic tubes, followed by glass models designed to mimic the size and geometry of the coronary vasculature. The product may experience a series of changes resulting from these tests until the designer is satisfied with performance, and once a certain level of confidence is achieved the testing will proceed to the next available model. In the medical device industry this model is generally a live animal.

In practice, the medical device industry typically employs one or more of the four previously mentioned (Table I) model types in simulation testing prior to seeking approval for human use (a clinical trial). Of course, common sense dictates that the model selected be representative of actual use conditions, but only the clinical trial, which is not a simulation test, fully satisfies this criteria. Unfortunately, human subjects are unavailable for use until late in the development cycle due to risk, regulatory, and ethical considerations. A live animal model has therefore traditionally been the next best choice.

Animal models are currently the gold standard of pre-clinical trial medical device simulated use testing. In fact, the quality of data produced in these studies can be very high, particularly if the proper animal model is selected, the device and protocol are well designed, and the correct number of animals is used. Designed experiments are possible and are commonly employed, but require an increase in the number of animals. These tests are also performed under physiological (for the animal) conditions. Unfortunately, these studies are expensive because of the staff and facilities required to support the work. A registered facility must be contracted to run the study and care for any animals purchased, a surgeon must be retained to perform the required procedures and to generate the study protocol, and the services of a veterinarian, anesthesiologist, and surgical aide are also required. These studies can easily exceed $100,000 in total costs, and grow even more costly as the number of animals is increased.

The inability to test prototype devices on human subjects is the reason medical device developers resort to animal studies in the first place. Still, animal models suffer from a whole range of unique problems, including the many deviations between human and animal anatomy and physiology, the confounding effects of variation between individual animals, and the unpredictability that arises from using a model that is extraordinarily complex.

Animal models may include live canine, porcine, or bovine specimens, among others. While these animals do offer an in vivo environment, their anatomy and physiology differs significantly from that of a human. The great expense and specialized facilities required limit their in-house use. Reproducibility may also be an issue as both inter- and intrasubject variability are difficult to control. Additional considerations include contention with the Animal Welfare Act, the significant expense associated with contracting regulated facilities and medical practitioners, and the risks related to handling biohazardous materials.

To get around these issues, developers tend to gravitate toward simpler and more accessible models such as cadavers and benchtop fixtures. Unfortunately, there tends to be an inverse relationship between the usefulness and complexity of the model employed. For example, cadaver tissues provide an accurate representation of anatomical geometry, but the required chemical preservation greatly alters the physical properties of the tissues. In addition, biological temperatures and flows cannot generally be simulated, subjects are difficult to source and maintain in useful quantities, and an educational institution must almost always be contracted (at considerable expense) to perform the study.

These factors drive early stage medical device developers to simple benchtop fixtures made (usually) in house by the developer. Unfortunately, these models are typically designed by individuals lacking an understanding of anatomy and physiology, and are usually fabricated from typical engineering materials such as metal, glass, and plastic. While an argument may be made that these models are better than nothing, they are certainly not representative of actual use conditions. Furthermore, engineers in general will agree that the quality of test data is dependent on the good logic behind the test protocol and the quality of the model employed. A poor model is therefore more likely to yield misleading data, and a design based at an early stage upon this data is more likely to require correction at a later stage in development.

SUMMARY

The use of a poorly conceived model in development testing will lead to reduced product quality, increased development costs, and greatly lengthened product timelines. Fortunately, these failures may be avoided by employing an intelligent development scheme in conjunction with a high quality model. Accordingly, the subject invention pertains to complex synthetic anatomical models that are designed to enable simulated use testing by medical device companies, medical device designers, individual inventors, or any other entity interested in the performance of medical devices, and in particular those that generate electromagnetic radiation. These models are unique in possessing a level of complexity that allows them to be substituted for either a live animal, an animal cadaver, or a human cadaver in the testing of these devices. These models are further characterized by a similarity of geometry, individual component physical properties, and component-to-component interfacial properties with the appropriate target tissue and anatomy.

In certain embodiments, the subject invention pertains to models that comprise components made of tissue analog materials that are designed to simulate dielectric properties of human or nonhuman animal tissue. Such embodiments will allow the testing of the affect of electromagnetic radiation produced by certain devices, equipment, or even electromagnetic radiation produced in the environment on tissue. In a specific embodiment, the model comprises components made of tissue analog materials designed to simulate dielectric properties of neural tissue.

These and other advantageous aspects of the subject invention are described in the detailed description below, description of the drawings, and the appended claims.

DEFINITIONS

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

The term "artificial" as used herein to describe a model component refers to a component that is either synthetically manufactured or naturally manufactured in vivo and assembled with other model components. In the case of naturally manufactured artificial components, this may refer to actual tissues or anatomical structures procured from a cadaveric human or from a nonhuman subject that are removed from the subject processed and assembled with other artificial components.

The term "tissue analog material(s)" as used herein refers to a material or combination of materials designed to simulate one or more physical characteristics (properties) of a relevant living target tissue. Analog materials used to design tissue analog materials may include, but are not limited to, hydrogel, interpenetrating polymer networks, fibers, silicone rubber, natural rubber, other thermosetting elastomers, other thermoplastic elastomers, acrylic polymers, other plastics, ceramics, cements, wood, styrofoam, metals, actual human tissues, actual animal tissues, and any combination thereof. For model embodiments comprising one or more components, each component part may be constructed from one or more tissue analog materials.

The tissue analog materials are formulated to simulate one or more physical characteristics of a target living tissue. These physical characteristics include, but are not limited to, uni-axial or multi-axial tensile strength or modulus, uni-axial or multi-axial compressive strength or modulus, shear strength or modulus, coefficient of static or dynamic friction; surface tension; elasticity; wettability; water content; electrical resistance and conductivity; dielectric properties; optical absorption or transmission, thermal conductivity, porosity, moisture vapor transmission rate, chemical absorption or adsorption; or combinations thereof. Each tissue analog material is designed so that one or more physical characteristics of the tissue analog material will sufficiently match the corresponding physical characteristic(s) of the relevant tissue on which the tissue analog material is based. More specifically, each tissue analog material is preferably formulated so that the physical characteristic(s) of the tissue analog fall within a range that is no more than 50% lesser or greater than the targeted physical characteristic(s) of the relevant living tissue on which the tissue analog material is based.

The aforementioned listed physical characteristics are well understood, and may be determined by well-established techniques. References teaching the determination of different physical characteristics (in no way intended to be an exhaustive list) include the following:

(1) Shigley, J. E., and Mischke, C. R. *Mechanical Engineering Design*, 5$^{th}$ Ed., McGraw-Hill, 1989.

(2) Harper, C. A., *Handbook of Materials for Product Design*, 3$^{rd}$ Ed., McGraw-Hill, 2001.

(3) Askeland, D. R., *The Science and Engineering of Materials*, 2$^{nd}$ Ed., PWS-Kent, 1989.

(4) LaPorte, R. J., *Hydrophilic Polymer Coatings for Medical Devices*, Technomic Publishing, 1997

(5) Hayt, W. H., and Kemmerly, J. E., *Engineering Circuit Analysis*, 4$^{th}$ Ed., McGraw-Hill, 1986.

(6) Park, J. B., and Lakes, R. S., *Biomaterials, An Introduction*, 2$^{nd}$ Ed., Plenum Press, 1992.

(7) Lindenburg, M. R., Editor, *Engineer in Training Manual*, 8$^{th}$ Ed., Professional Publications, 1992.

Other references of note that are incorporated herein are Ottensmeyer et al., "The Effects of Testing Environment on the Viscoelastic Properties of Soft Tissues, Proceedings of Medical Simulation," *International Symposium*-ISMS 2004, Cambridge, Mass., Jun. 17-18, 2004 and references cited therein; and Brouwer et al. "Measuring in Vivo Anaimal Soft Tissue Properties for Haptic Modeling in Surgical Simulation", *Proc. Medicine Meets Virtual Reality*, Newport Beach, Calif., IOS Press, 2001, and references cited therein.

Particular teachings of certain physical characteristics are noted (references numbers related to preceding list):

Tensile strength and modulus, both measured in Pascal (Pa)—Ref 1, pg 186.

Compressive strength and modulus, both measured in Pascal (Pa)—Ref 2, pg 718.

Shear strength and modulus, both measured in Pascal (Pa)—ASTM Standard D3165-00, Standard Test Method for Strength Properties of Adhesives in Shear by Tension Loading of Single-Lap-Joint Laminated Assemblies.

Coefficient of static and dynamic friction, a dimensionless number—Ref 7, pg 445.

Surface tension, measured in dynes/cm—Ref 6, pg 57.

Wettability, measured in terms of contact angle (degrees)—Ref 4, pg 3.

Water content, measured in mass percent (%)—Ref 4, pg 41.

Electrical resistance and conductance, measure in ohm for resistance and mho for conductance—Ref 5, pg 25.

Dielectric properties, measured in various units—ASTM Standard E2039-04 Standard Test Method for Determining and Reporting Dynamic Dielectric Properties.

Optical absorption and transmission, measured in $cm^{-1}$—Ref 3, pg 739.

Thermal conductivity, measured in cal/(cm-s-C)—ASTM Standard D5930-01 Standard Test Method for Thermal Conductivity of Plastics by Means of a Transient Line-Source Technique.

Porosity, measured in volume percent (%)—Ref 3, pg 490.

Moisture vapor transmission rate, measured in $g/(mil-in^2)$—Ref 2, pg 941.

The term "hydrogel(s)" as used herein refers to a unique class of materials that contain a large amount of water and generally exhibit a high degree of elasticity and lubricity. These materials are ideal for simulating the physical properties of many living soft tissues. Hydrogels are materials that are wetable and swell in the presence of moisture and retain water without dissolving. These materials are generally constructed of one or more hydrophilic polymer molecules, although copolymerization with hydrophobic monomers may also lead to the formation of a hydrogel. These materials are generally elastic, and exhibit a three-dimensional network that is either crosslinked directly by chemical bonds or indirectly through cohesive forces such as ionic or hydrogen bonding.

The "data value" as used herein refers to a numerical value that is representative of a measurement of one or more physical characteristics. The numerical value is typically provided in a unit of measurement obtained from observation of a specimen under a defined set of conditions. The simulation of physical characteristics seeks to closely correlate a data value of a target tissue with that of a tissue analog material. This may be expressed by a percentage a data value obtained from a tissue analog material is greater or lesser than a data value obtained from a target tissue.

The term "geometrically mimic" as used herein refers to a comparative relationship of a configuration of an artificial anatomical model, and/or artificial structural component thereof, with a target anatomical structure wherein such configuration comprises one or more similar geometric features of the target anatomical structure to be mimicked, such as length, width, diameter, thickness, cross-section, and/or, in most cases general shape of a particular target anatomical structure.

The term "human or non-human animal tissue" as used herein refers to the one or more tissues that constitute a human or non-human animal anatomical structure.

As used herein the term "human or non-human animal anatomical structure" refers to one or more tissue structural components that make up a part of anatomy of a human or non-human animal. A part of anatomy may include, but is not limited to, whole organs, parts of an organ, or a section of a body comprising one or more tissue types, organ types, and/or part of organ(s).

In certain model embodiments, one or more components may be cooperative with other one or more components. The term cooperative in this context means that such cooperative components are contiguous, engaged, or integrated with one another. Further, components cooperative with one another may be designed to be dissociable, i.e., removably cooperative.

In certain model embodiments, one or more components may be cooperative with other one or more components. The term cooperative in this context means that such cooperative components are contiguous, engaged, or integrated with one another. Further, components cooperative with one another may be designed to be dissociable, i.e., removably cooperative.

DETAILED DESCRIPTION

There is much interest in the implementation of electromagnetic radiation producing medical devices to assist those who have experienced neurological trauma or disease to restore function lost by such trauma or disease. For example, medical device implants have been developed that serve to restore hearing to those with auditory dysfunction, typically brought about by mechanical or nerve damage. Such devices provide an electrical pulse to either certain nerves or directly to parts of the brain in response to sounds. Scientists and engineers envision that similar approaches may be implemented to help restore motor function or other senses lost due to neurological injury. It is not difficult to imagine the implementation of such devices to restore one's ability to walk after suffering from a spinal cord trauma. One obstacle to the development of such technologies is the ability to easily and cost-effectively test the effects of such devices on healthy tissues. Studies to predict the effects of the continued application of electromagnetic radiation are difficult and expensive to conduct, but when live patients are involved the studies often yield inconclusive results, and of course ethical concerns prevent more thorough testing. As an alternative to using these patients, a bench top model may be employed to physically simulate the insult to the tissue as a relatively inexpensive, easily repeatable, and logical first step before resorting to animal studies. However, for this approach to be productive, the model employed must be representative of the actual target anatomy and tissue physical characteristics in which the medical device will normally be used.

In certain embodiments, the subject invention pertains to models simulating the dielectric properties of human or non-human animal tissues. Such embodiments are designed to enable simulated use testing by medical device companies, medical device designers, individual inventors, or any other entity interested in the performance of medical devices, equipment, etc, and the affects of such devices on tissues. Alternatively, embodiments of the subject invention may be used by consumer safety groups to study deleterious effects that may be caused by electromagnetic radiation producing consumer items, such as cell phones, microwave ovens and the like, or environmental conditions such as power lines. These models are unique in possessing a level of accuracy in simulating properties of tissues that allows them to be substituted for either a live animal, an animal cadaver, or a human cadaver in the testing of these devices. These models are further characterized by a similarity of geometry, individual component physical properties, and component-to-component interfacial properties with the appropriate target tissue and anatomy.

The model embodiments of the subject invention create a test environment similar in many ways (mechanical properties, physical properties, temperature, flow rate, viscosity, etc) to that of a living animal. In addition, individual tests may be repeated as many times as desired under identical or (if desired) altered conditions. Also, the tissue-contacting portion of the model may be removed to allow a quasi-histological examination to be performed after each test, an important feature that allows the engineer to predict the tendency of a particular device to inflict injury (or other effect) on the patient.

A study employing the models of the subject invention allows the generation of data that is comparable, and in some ways superior to that of an animal study. Furthermore, since these studies employ a reproducible model, the statistically confounding effect of variation between animals is eliminated. The ability to perform truly reproducible tests allows interactions between the device and the model, as well as interactions between multiple design parameters to be evaluated, a task which is nearly impossible with an animal study. In addition, the expense related to the purchase and housing of animals, contracting registered facilities, and retaining medical practitioners is eliminated. The risks associated with biohazards are also eliminated and a number of innocent animals are spared.

Benchtop fixtures are sometimes designed to mimic the general size and geometry of a target tissue, and the best of these are also designed to work at body temperature in the presence of fluids. However, the typical use of engineering materials in their construction makes these common models dissimilar to the target anatomy and calls into question the value of any data collected using them, even when designed experiments are employed. In addition, these models may only be used to predict device performance, not the effect of the device on the target tissue.

In comparison, the model embodiments of the subject invention enable for the first time a potentially large number of tests to be completed and repeated under identical conditions in an environment that is both geometrically, mechanically, and physically similar to the target anatomy. An engineering technician may perform these tests on a simple benchtop setup, while still generating very high quality of data. Also, because this data is provided early in the development process, design errors may be discovered earlier; leading to a shorter development cycle and a reduced development budget. Finally, since the effect of the device on the target tissue can be predicted, device quality is improved.

Available cadaver models can, provide a fair representation of anatomical geometry, but the mechanical and physical properties of the target anatomy are altered by preservation techniques. It is impossible to use these models at normal body temperature or in the presence of test fluids, and they cannot be employed to accurately predict the physical effect of the device on the target issue. An educational institution must generally be contracted, along with a principal investigator, to perform the study, and since the specimens are difficult to source it is common to run only a single test. Biohazards are an additional risk.

In comparison, the model embodiments of the subject invention facilitate the generation of animal study quality data using a simple benchtop setup that can be used by an engineering technician. These models may be used at body temperature in the presence of any real or simulated physiologic fluid, and since the device contacting portions of the model may be removed and replaced, an unlimited number of tests may be performed. The need to contract with research facilities, employ costly medical practitioners, and expose staff to the risks associated with biohazards are eliminated.

The models of the subject invention are characterized by a similarity of geometry, of individual component physical properties, and of component-to-component interfacial properties with living tissue. On the simplest level, individual model components are fabricated such that they mimic the geometry of a particular target anatomy.

The geometric data needed for fabrication is typically obtained in two ways. The traditional approach is to obtain data from the literature on morphology or from cadaver measurements. While not a bad approximation, this method is time-consuming and permits a large degree of error. A better method would be to get the geometric data directly from a patient or from sources such as the Visible Human Project.[2]

After collecting the appropriate geometric data, the individual model components may be fabricated from appropriate analog materials. Depending on the complexity of the part and the type of materials used, the individual component might be molded, extruded, or machined. For complex geometries, however, these techniques may become cumbersome and expensive. In these cases rapid prototyping techniques such as stereolithography offer a relatively inexpensive alternative. Techniques are being developed that allow actual patient data (obtained from MM or spiral-CT images) to be fed directly into the rapid prototyping system, thus replicating the patient's anatomy exactly. This technology allows for the production of extremely realistic simulations.

Certain embodiments of the subject invention are constructed from multiple components, and these individual components are fabricated in such a way that they mimic the geometry (length, width, diameter, thickness, cross-section, shape, etc) of a particular portion of the target anatomy that is relevant to the medical device under test.

The individual components of the subject invention are assembled in such a way that the interaction between adjacent components yields the overall interaction expected in the actual target tissue. That is, the interfacial properties (bond strength, component-to-component friction, etc) between the various model components are designed to simulate the interaction between the relevant tissues in the target anatomy.

The first design parameter typically entails selecting physical properties that are important for the analog material to mimic in the decided application. These properties will vary depending on the type of device under test, the target anatomy, and the general objective of the testing. Any number of properties may be included in the target properties list, but it should be noted that as this list gets longer it becomes progressively more difficult to satisfy all of the design requirements. In fact, in typical embodiments, if a particular component requires an analog material with more than three target properties it might be better to separate the components into multiple parts.

The second design parameter typically involves selecting the source of the physical properties data. That is, it should be determined if the model will be based on human or animal (or both) tissue properties. Once this is determined, the data may either be drawn from the literature or generated directly by performing the appropriate physical tests on actual samples of the target tissues. The most common tissue sources for non-human properties tests are the sheep and pig, but other animal sources are possible as well.

The data collected from this testing regime will be used as a target in the design of the analog materials, and the design intent is that these analog materials exhibit physical properties that mimic the physical properties of the target tissue samples. After the materials are formulated their performance will be verified by repeating the same physical properties tests that were performed on the original tissue samples on the newly formulated analog material samples. Of course, these tests must be performed under conditions as reasonably similar as possible to the original (tissue sample) tests.

Part of the design process involves prioritizing the various target properties for the synthetic analog materials. Less important properties should be placed further down the list and given a lower priority during the formulation process. This is typically, though not necessarily, required because the design becomes progressively more difficult to produce as the number of modeled properties increases. The number of target properties are preferably limited to three or fewer. If more complex model behavior is required than this restriction will allow, then the number of components can be increased instead. For example, the artery might by constructed from three two-property analog materials instead of one three-property analog. Typically, a component comprised of several analogs will exhibit a more complex (and realistic) response than a component constructed from a single (multi-property) analog.

Typical engineering materials, including many metals, ceramics, and plastics commonly employed in industry may be used depending on the required analog properties. However, in cases where soft tissues are being modeled it will generally be advantageous to use nonstandard materials such as hydrogels. These materials swell in the presence of moisture and can retain large amounts of water without dissolving. They are constructed of one or more hydrophilic polymer molecules, although copolymerization with hydrophobic monomers may also lead to the formation of a hydrogel. These materials are generally elastic, and exhibit a three-dimensional network that is either crosslinked directly by chemical bonds or indirectly through cohesive forces such as ionic or hydrogen bonding. Hydrogels are particularly advantageous in this application because the formula may be manipulated to give a combination of water content, lubricity, abrasion resistance, and other properties characteristic of living soft tissues. In this respect these materials are particularly suited to modeling fragile tissues such as venous or arterial intima and ciliated epithelia. Hydrogels also provide an ideal substrate for maintaining a surface of live cells if so desired.

The models of the subject invention may employ a wide variety of hydrogel materials, including but not limited to polyvinyl alcohol, polyvinyl pyrrolidone, polyethylene oxide, polyhydroxyethyl methacrylate; polyethylene glycol, hyaluronic acid, gelatin, carrageen, alginates, agar, chondroitan sulfate, dermatan sulfate (and other proteoglycans). This entire class of materials is physically more tissue-like simply by nature of incorporating water, but by carefully controlling such parameters as molecular structure, density, wall thickness, durometer, and many other physical properties and characteristics a good match between the actual tissue and analog material may be achieved.

Poly(vinyl alcohol) is normally produced by the acid-catalyzed hydrolysis of poly(vinyl acetate), which effectively converts the pendant acetate groups to hydroxyl groups. The properties of the resulting polymer are determined by tacticity, degree of hydrolysis, and molecular weight. Most commercial grades of PVA are stereoregular (primarily isotactic) with less than 2% of the repeat units forming in the 'head-to-head' (adjacent hydroxyl groups) configuration. In theory this should allow a high degree of crystallinity in the finished product. However, this is hindered by the presence of residual acetate groups so the tendency toward crystallization depends primarily on the degree of hydrolysis. This refers to the percentage of converted acetate groups on the main chain. Partially hydrolyzed grades (less than 75% conversion) do not crystallize significantly and are soluble in water at room temperature. This is because the large number of bulky acetate groups increases free volume and prevents the long-range interchain associations required for crystallization to occur. As the degree of hydrolysis increases the loss of bulky acetate groups reduces free volume and the chains are allowed to more closely approach one another. The compact but highly polar hydroxyl groups then come into close proximity and 'bind' the chains together through strong hydrogen bonding. These interchain forces increase the degree of crystallinity and greatly reduce solubility. In fact, in spite of the high concentration of hydroxyl groups completely hydrolyzed grades of PVA should be heated to nearly 100 C to attain solution. These materials exhibit excellent mechanical properties and chemical resistance and also swell to a significant degree.

The properties of PVA hydrogels vary with molecular weight, but since these materials are normally obtained in polymer form the molecular weight cannot easily be adjusted. Instead these properties are typically modified by means of chemical or physical crosslinking. Chemical gels are easily formed by the addition of agents which undergo condensation with the hydroxyl groups on the main chain. A number of aldehydes (glutaraldehyde, formaldehyde, etc.), dicarboxylic acids (adipic acid, terephthalic acid, etc.), and metal ions ($Fe^{3+}$, $B^{5+}$, etc.) will form chemical bonds with PVA which result in crosslinks. Longer molecules such as diacids are generally preferred over metal ions because the ion 'bridge' is short and restrictive, embrittling the material. Molecules such as adipic acid can effectively restrict chain mobility while maintaining some measure of flexibility.

Validation of embodiments of the subject models is, in most cases, a desired objective. First, it will help determine the degree of realism of the simulation—in other words, how accurately the simulation performs compared to the in vivo environment. If the intent is to simulate blood flow in the carotid artery, for example, one type of validation would reveal how flow rate in the simulation compares to the flow rate in the patient.

Validation also identifies the limitations of the simulation. Especially in theoretical simulations, it is important to understand not only the accuracy of the model but also the circumstances under which it breaks down. A simulation might be highly accurate under normal situations, but if an abnormality is introduced, the simulated results might not be representative of a similar abnormality in vivo. Finally, if data from the simulation will be used in support of an FDA submission, it is even more important that the simulation be validated. The stronger the validation, the stronger the submission.

In general, three validation strategies are available: quantitative, qualitative, and indirect. Quantitative validation involves collecting numerical data from the simulation and comparing it to data collected in vivo under similar conditions. Collecting quantitative data usually involves the use of instrumentation—for example, pressure transducers to record simulated blood pressure. Common diagnostic technologies such as ultrasound or MRI might also be used. Of course, technologies such as ultrasound are designed for use on biological tissue, and since the simulation will probably be made of inert materials, some modifications may be necessary, as those skilled in the art will appreciate in view of the teachings herein.

In qualitative validation, experienced users (usually clinicians) use the device in the simulation following the same protocols they would follow when using the product in a patient. After the simulated procedure, users convey in as much detail as possible how the device performed in comparison to their experience of using a comparable device in a patient. To test a new product, the manufacturer should identify current users of similar products. For obvious reasons, users having the most clinical experience will typically yield the best results. When used properly, the "touchy-feely" data generated in the qualitative validation are as important as the numerical data obtained from the quantitative validation.

Indirect validation involves the comparison of physical performance data from the model to the actual use environment. This is the type of validation that is integral to the design process for Animal Replacement Models. The basic logic behind this form of validation is that if the individual model components exhibit properties similar to the target tissues then the model as a whole will exhibit performance similar to the synthetic organ being constructed. This type of validation will typically be followed by other tests once the model is completely constructed.

A strong validation strategy involves a combination of all of these techniques. Conducting only one type of validation leaves open the possibility that some important piece of information has been missed. When used together, the results help maximize the accuracy and degree of realism of the simulation.

The model embodiments of the subject invention comprise features that make them valuable for medical device design and development testing. First, since the models are designed to respond to physical stimulus in a fashion similar to the target (human or animal) anatomy, device performance in the model may be used to predict device performance in the target anatomy. Second, the device interfacing portion of the model may be removed for quasi-histological examination, allowing the effect of the device on the target anatomy to be measured. This is particularly important because it allows the potential for injury to be predicted. Third, because the device interfacing portion of the model can be removed and replaced, a large number of tests can be performed under either identical or varying conditions as desired. This would allow the generation of descriptive statistics on device performance and the execution of meaningful designed experiments, both of which are impossible with live animals or cadavers. Fourth, if a hydrogel substrate is employed to support a living tissue bed, the effect of the test device on actual living cells can be predicted. Fifth, the models may be equipped with pumps, heaters, and other accessories to more accurately model almost every aspect of actual use conditions. Sixth, the models may be equipped with sensors that allow the measurement of device influences such as applied force and pressure on portions of the target anatomy. Also, these models provide a wide range of cost, safety, and logistical benefits to device developers compared to existing benchtop models, cadavers, and live animals.

Description of the Illustrative Embodiments

Figure 1:
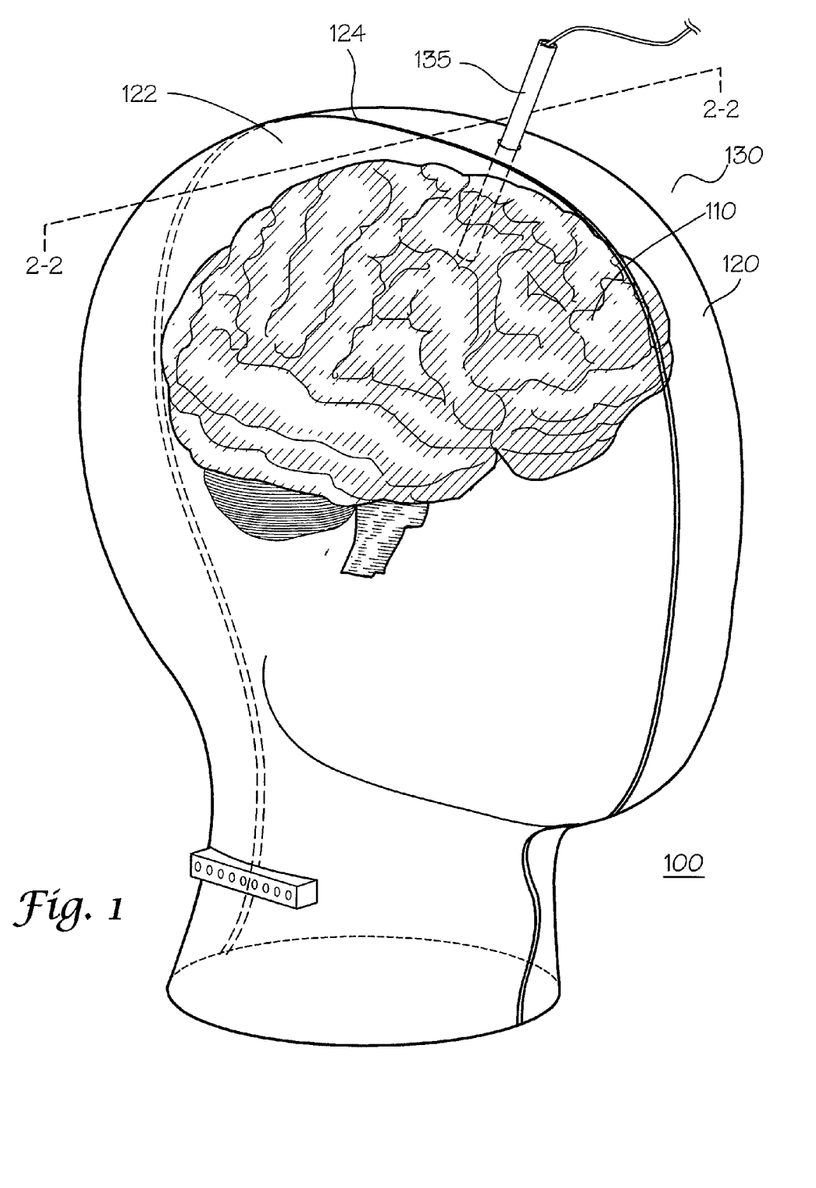
FIG. 1 shows a perspective view of a head model comprising components simulating dielectric properties of brain.

Turning to FIG. 1 a perspective view of a dielectric properties model 100 is shown. The model 100 comprises an artificial brain component 110 that is made of a tissue analog material that simulates the dielectric properties of brain tissue. The artificial brain component 110 is contained within an artificial cranial encasing 130. The encasing 130 is comprised of two sections 120 and 122 that are removeably engaged from one another along seam 124. This allows the user to readily replace the artificial brain component 110 or to manipulate the brain component 110 such as by implantation of a probe 135 designed for studying the affect of an electromagnetic radiation producing object on the artificial brain component 110. For example, the probe may sense current in the artificial brain component caused by the electromagnetic radiation producing object. The probe 135 is a plunge probe that may be inserted into the model at any suitable location for studying effects of electromagnetic radiation on the artificial brain component 135. It is noted that any number of commercially available probes could be implanted into the artificial brain component 110 for this purpose.

Figure 2:
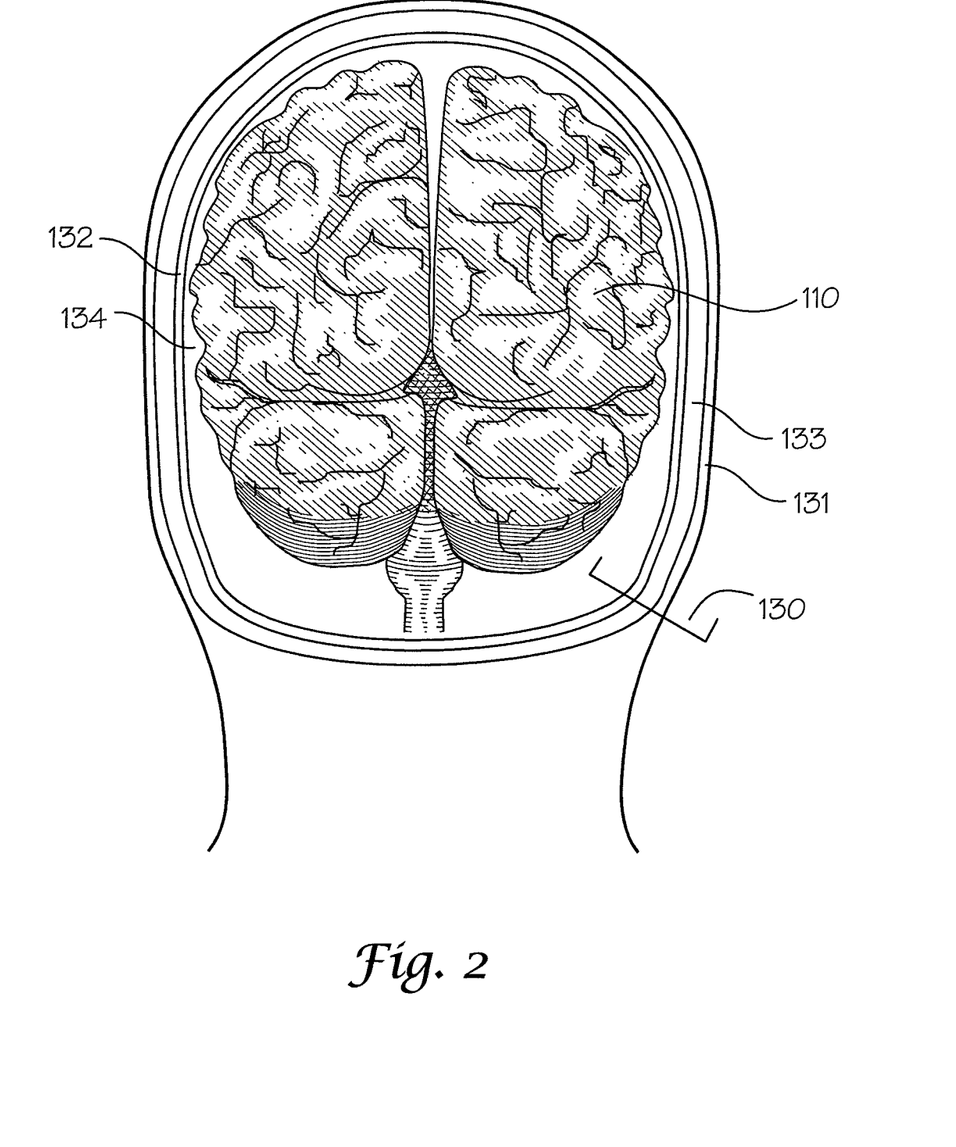
FIG. 2 shows a cross-sectional view at axis X-X indicated in FIG. 1.

FIG. 2 shows a cross-sectional view of the model shown in FIG. 1 along the X-X axis. The encasing 130 is comprised of different layers to geometrically mimic the layers of a cranium. The encasing comprises a thin artificial skin layer 131 on its exterior. Immediately subjacent to the artificial skin layer 131 is an artificial bone layer 133 comprised of a tissue analog material designed for simulating at least one physical characteristic of cranial bone. Immediately subjacent to the artificial bone layer is an artificial membrane layer 132 comprised of a tissue analog material designed for simulation of at least one physical characteristic of one or more meninges. The membrane layer 132 may be comprised of three sub-membranes simulating physical characteristics of dura mater, arachnoid and the pia mater. Immediately subjacent to the artificial membrane layer 132 is a space comprising a fluid 134 comprised of a material designed for simulating at least physical characteristic of cerebrospinal fluid. The artificial brain component 110 is wetted by the fluid 134.

Figure 3:
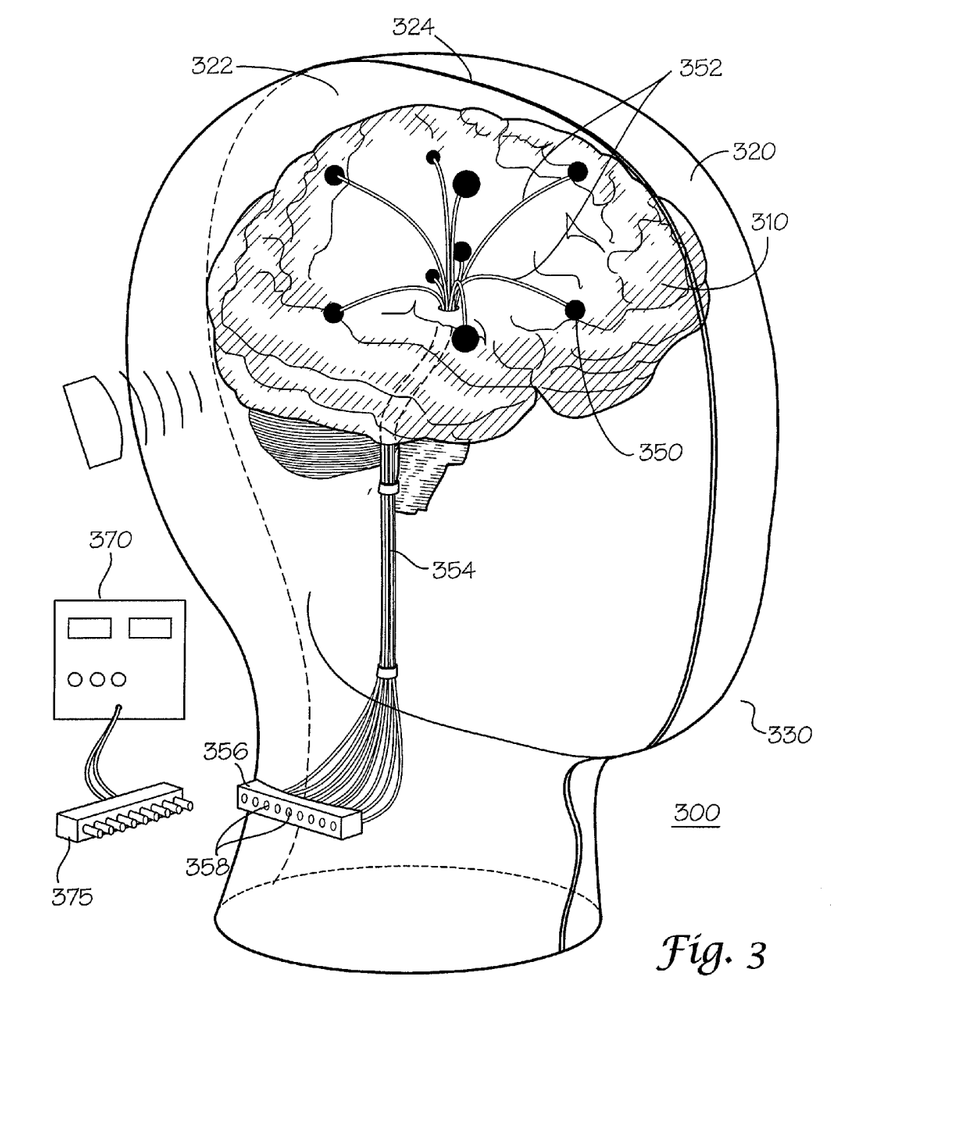
FIG. 3 shows a perspective view of a head model comprising electrode components to assist in measuring affects on brain.

FIG. 3 shows a perspective view of another model embodiment 300 of the subject invention. The model 300 comprises an artificial brain component 310 that is made of a tissue analog material that simulates the dielectric properties of brain tissue. The artificial brain component 310 is contained within an artificial cranial encasing 330. The encasing 330 is comprised of two sections 320 and 322 that are removeably engaged from one another along seam 324. FIG. 3 also shows a window into the interior of the brain component 310 which reveals an array of electrodes 350 disposed at locations within the brain component 310. The electrodes 350 are electrically connected to wires 352 which are brought together in a bundle 354 under the brain component 310. An adapter 356 is electrical connected to the bundle 354 which comprises electrical connections 358 to the respective wires 352. The adapter 358 will allow for the facile connection to an instrument 370 for studying phenomena sensed by the electrodes 350, such as current, which may comprise a corresponding adapter 375 that is cooperative with adapter 356. Such instrument and techniques for measuring as that taught by Gernot Schmid et al 2005 *Phys. Med. Biol.* 50 4711-4720 may be adapted to study phenomena in dielectric properties model embodiments. Such phenomena may be caused by an electromagnetic radiation device 360 placed in proximity with brain component 310. Device 360 may be placed exterior to cranial encasing 330, as shown, or within casing 330, or at a location on or within the brain component 310.

Figure 4:
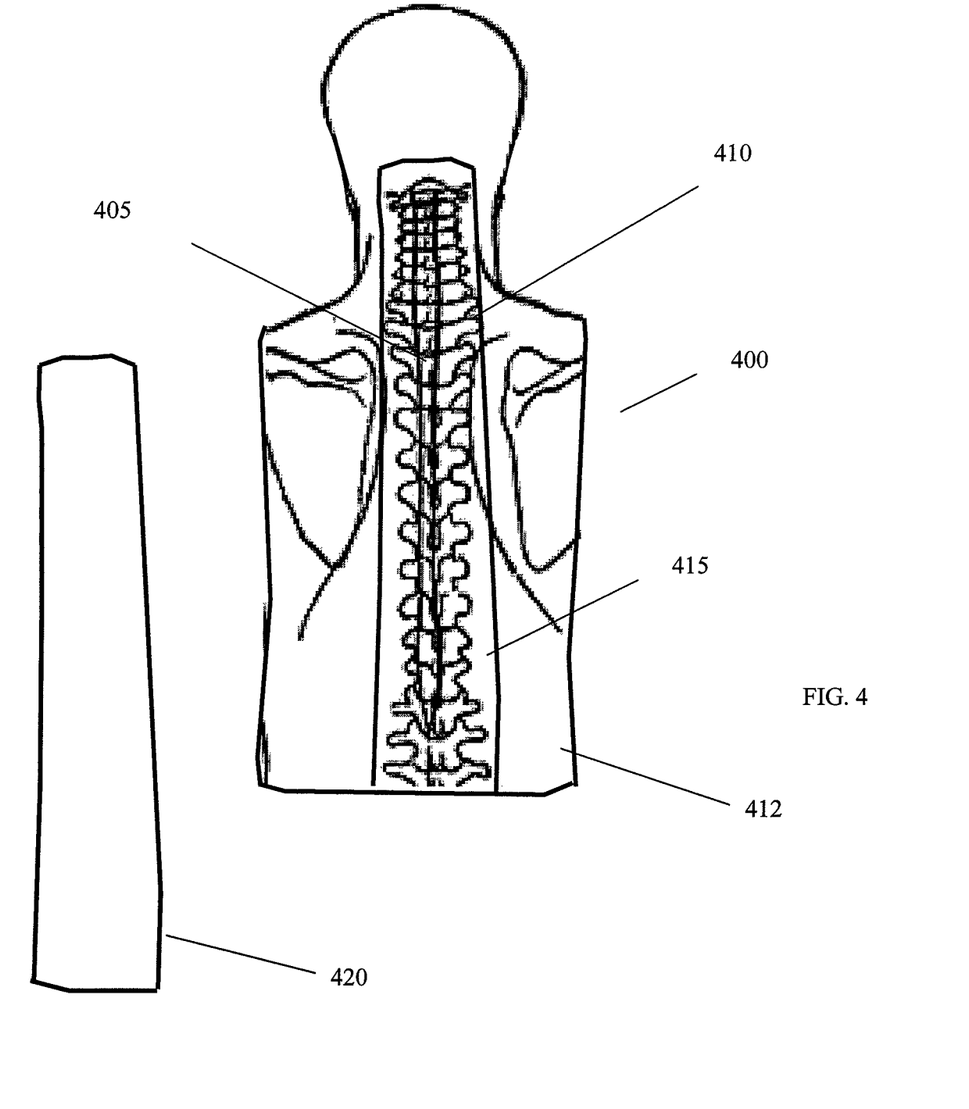
FIG. 4 shows a dorsal view of a spine model with vertebrae and spinal cord.

FIG. 4 shows a dorsal view of a spinal cord model 400. The model 400 comprises an artificial spinal column 410 made of tissue analog material that simulates bone. The spinal column 410 comprises a channel defined therein that comprises an artificial spinal cord 405. The spinal cord 405 is comprised of hydrogel material that is designed to simulate a dielectric property of living spinal cord tissue. The model comprises a casing 412 which comprises a cavity 415 into which the spinal column 410 and spinal cord 405 are disposed. The casing may be comprised of any suitable tissue analog material. A removable flap 420 covers the cavity 415. As discussed above in relation to FIG. 3, the spinal cord may comprise probes (not shown) and wires connected thereto (not shown) to assist in carrying out dielectric studies of the artificial spinal cord 405.

EXAMPLE 1

Calculation of Dielectric Properties

The determination of dielectric properties of tissues is necessary to design appropriate tissue analog materials that closely simulate such properties. According to a specific embodiment, the conductivity [S/m] and the relative permittivity of tissues so that appropriate tissue analog materials can be fabricated. One can determine this by conducting an evaluation of a human or nonhuman tissue, such as by the techniques taught at http://www.brooks.af.mil/AFRL/HED/hedr/reports/dielectric/Report/Report.html; or K R Foster et al 1979 *Phys. Med. Biol.* 24 1177-1187. Alternatively, one can based the design of tissue analog materials on dielectric property values previously determined and publicly available. A recent compilation of Gabriel et al. covers a wide range of different body tissues and offers equations to determine the appropriate dielectric values at each desired frequency. C. Gabriel, S. Gabriel, and P. Mason. Compilation of the Dielectric Properties of Body Tissues at RF and Microwave Frequencies http://www.brooks.af.mil/AFRL/HED/hedr/reports/dielectric/Title/Title.html, 1999.

Using the given formulas in Gabriel et al., the dielectric properties for each tissue at 8.25 MHz, 42.6 MHz and 64.0 MHz were calculated. The values are given Table 2. It is also helpful to evaluate the SAR and the heating of the body tissues, as a function of density $\rho$ [kg/m$^3$] and the specific heat $c_s$ [J/kg $^\circ$ K]. The data compiled from the literature are given in Table 1. Om P. Gandhi, G. Lazzi, and C. M. Furse, Electromagnetic Absorption in the Human Head and Neck for Mobile Telephones at 835 and 1900 MHz, *IEEE Trans. on Microwav. Theo. and Techn.*, 44(10), October 1996; L. A. Geddes and L. E. Baker, The specific resistance of biological material—a compendium of data for the biomedical engineer and physiologist, *Med. & Biol. Eng.*, 5:271-293, 1967; F. B. Sachse, M. Müller, M. Glas, and K. Meyer-Waarden, Segmentation and tissue-classification of the Visible Man Dataset using the computertomographic scans and the thin-section photos, In *Proc. 1st Users Conference of the National Library of Medicine's Visible Human Project*, Bethesda, Md., pages 125-126, 1996. Table 1 also provides the material numbers and the corresponding tissue types.

For the saline phantom the conductivities of saline solution at different concentrations have been compiled from Geddes and Baker and are given in Table 3. The saline concentration given is related to the mass of the sodium chloride in the solution, i.e. a concentration of 1% means 10 g sodium chloride per liter water.

TABLE 1

Physical properties of human tissue and electrode material: density $\rho$ [kg/m$^3$] and specific heat $c_s$ [J/(kg $^\circ$ K)].

| Mat. nr. | Tissue Type | $\rho$ [kg/m$^3$] | $c_s$ [J/(kg $^\circ$ K)] |
|---|---|---|---|
| 1 | bone marrow | 1810 | 1256 |
| 2 | fat | 920 | 2973 |
| 3 | bone | 1810 | 1256 |
| 4 | white matter | 1040 | 3664 |
| 5 | grey matter | 1040 | 3664 |
| 6 | skin | 1010 | 3662 |
| 7 | eye | 1170 | 3664 |
| 8 | muscle | 1040 | 3639 |
| 9 | blood | 1060 | 3894 |
| 10 | CSF | 1010 | 4182 |
| 11 | nerve tissue | 1040 | 3664 |
| 12 | lens | 1100 | 3664 |
| 13 | optical nerve | 1040 | 3664 |
| 14 | cartilage | 1100 | 3664 |
| 15 | PtIr(10%) | 21570 | 130 |
| 16 | PTFE | 2150 | 1010 |

TABLE 2

Dielectric properties of human tissue and electrode
material: conductivity σ [S/m] and relative permittivity
$\epsilon_r$ for 8.25 MHz, 42.6 MHz and 64.0 MHz.

| Mat. nr. | σ [S/m] | $\epsilon_r$ |
|---|---|---|
| 1 | 0.120/0.149/0.154 | 59.0/19.8/16.4 |
| 2 | 0.051/0.064/0.066 | 32.3/15.1/13.6 |
| 3 | 0.041/0.056/0.060 | 41.7/18.6/16.7 |
| 4 | 0.149/0.261/0.292 | 190.5/82.9/67.8 |
| 5 | 0.271/0.466/0.511 | 357.5/121.9/97.4 |
| 6 | 0.172/0.386/0.436 | 417.1/119.1/92.2 |
| 7 | 0.789/0.863/0.883 | 248.1/86.3/75.3 |
| 8 | 0.610/0.672/0.688 | 198.0/80.9/72.2 |
| 9 | 1.083/1.184/1.207 | 341.1/100.6/86.5 |
| 10 | 2.002/2.035/2.066 | 108.7/102.8/97.3 |
| 11 | 0.215/0.290/0.312 | 178.8/65.3/55.1 |
| 12 | 1.020/0.270/0.286 | 400.0/57.8/50.3 |
| 13 | 0.215/0.290/0.312 | 178.8/65.3/55.1 |
| 14 | 0.360/0.433/0.452 | 211.6/72.8/62.9 |
| 15 | $3.125 \cdot 10^6$ | 1.0 |
| 16 | $1 \cdot 10^{-16}$ | 2.1 |

TABLE 3

Conductivity σ [S/m] for the saline phantom
at different saline concentrations.

| Conc. [%] | 1 | 2 | 3 | 4 |
|---|---|---|---|---|
| σ [S/m] | 1.80 | 3.02 | 4.24 | 5.46 |

The relative permittivity was set to $\epsilon_r = 78$ for all simulated parameter sets.

EXAMPLE 2

Tissue Analog Material Simulating Dielectric Properties of Brain

Tissue analog materials comprised of hydrogels are typically employed to construct tissues in which dielectric properties are simulated. Provided below are examples of hydrogel formulations that may be used. It is noted that such hydrogel materials are typically doped with metal (aluminum, tin, or iron) and nonmetal (silicon or carbon) powders and/or salts, as appropriate, to achieve or alter the dielectric properties of a material depending on the tissue intended to be simulated.

In one embodiment, the hydrogel material is formed by admixing a monomer, water, and an initiator. The monomer polymerizes to form a polymer network. By way of example only, the admixture of components may comprise about 10 to about 50 percent, by weight, monomer; about 0.1 to about 5 percent, by weight, initiator, and about 45 to about 85 percent, by weight, water. In a specific example, the monomer used is n-vinyl pyrrolidone or hydroxyethyl methacrylate, or a combination thereof and the initiator used is ethyl 2,4,6-trimethylbenzoylphenylphosphinate (UV mediated). In a more specific example, the admixture comprises about 25 to about 30 percent, by weight, hydroxyethyl methacrylate; about 10 to about 15 percent, by weight, n-vinyl pyrrolidone; and about 55 to about 65 percent, by weight, water.

In another example, the hydrogel material is formed by admixing a polymer, water, and a cross-linking agent. By way of example only, the admixture may comprise about 5 to about 15 percent, by weight, polymer; about 1 to about 10 percent, by weight, cross-linking agent; and about 75 to about 95 percent, by weight, water. In a specific example, the polymer used is polyvinyl alcohol and the crosslinking agent used is glutaraldehyde. In a more specific example, the admixture comprises about 7 to about 9 percent, by weight, polyvinyl alcohol; about 11 to about 14 percent, by weight, glutaraldehyde; and about 78 to about 82 percent, by weight, water.

In a further example, the hydrogel material is formed by admixing a polymer, a monomer and an initiator. By way of example only, the admixture may comprise 10 to about 50 percent, by weight, monomer; about 5 to about 15 percent, by weight polymer; and about 35 to about 85 percent, by weight, water. In a specific embodiment, the monomer used is n-vinyl pyrrolidone or hydroxyethyl methacrylate, or combination thereof, and the polymer used is polyvinyl pyrrolidone. In a more specific embodiment, the admixture comprises about 25 to about 30 percent, by weight, hydroxethyl methacrylate; about 10 to about 15 percent, by weight, n-vinyl pyrrolidone; about 5 to about 7 percent, by weight, polyvinyl pyrrolidone; and about 55 to about 65 percent, by weight, water.

Finally, while various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims. The teachings of all patents and other references cited herein are incorporated herein by reference to the extent they are not inconsistent with the teachings herein.

What is claimed is:

1. A dielectric properties model comprising
a first artificial tissue component that geometrically mimics at least a portion of a human or nonhuman cranium such that said first component defines a cavity, said first component comprised of a tissue analog material that is designed to simulate at least one physical characteristic of bone;
a second artificial tissue component that geometrically mimics at least a portion of a human or nonhuman brain and is encased within, at least partially, said cavity, said second component comprised of a tissue analog material comprising hydrogel and designed to simulate a dielectric property of brain tissue, wherein said second component includes metal and nonmetal particles in an effective amount to simulate conductivity or permittivity of human or nonhuman animal tissue, said conductivity or permittivity is no more than 50 percent lesser or greater than that of human or nonhuman animal tissue; and
at least one membrane component surrounding said second artificial tissue component, said at least one membrane component comprised of a tissue analog material that simulates at least one physical characteristic of a meninx.

2. The model of claim 1, wherein said at least one membrane component comprises three adjacent membrane layers surrounding said second component, said three adjacent membrane layers comprised of tissue analog materials that simulate at least one physical characteristic of dura mater, arachnoid and pia mater, respectively.

3. The model of claim 1, wherein a space is defined between said at least one membrane component and said second component, said space comprising a fluid, said fluid comprised of a material designed to simulate at least one physical characteristic of cerebrospinal fluid.

* * * * *